(12) United States Patent
Tekulve (10) Patent No.: US 9,408,626 B2
(45) Date of Patent: Aug. 9, 2016

(54) CLOT REMOVAL SYSTEM AND METHOD

(71) Applicant: Kurt Tekulve, Ellettsville, IN (US)

(72) Inventor: Kurt Tekulve, Ellettsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 708 days.

(21) Appl. No.: 13/652,838

(22) Filed: Oct. 16, 2012

(65) Prior Publication Data

US 2013/0110082 A1 May 2, 2013

Related U.S. Application Data

(60) Provisional application No. 61/552,535, filed on Oct. 28, 2011.

(51) Int. Cl.
*A61B 17/3207* (2006.01)
*A61M 25/10* (2013.01)
*A61F 2/01* (2006.01)
*A61B 17/22* (2006.01)
*A61B 17/221* (2006.01)

(52) U.S. Cl.
CPC . *A61B 17/320758* (2013.01); *A61B 17/320725* (2013.01); *A61B 17/320783* (2013.01); *A61B 2017/2212* (2013.01); *A61B 2017/22051* (2013.01); *A61B 2017/22054* (2013.01); *A61F 2/013* (2013.01); *A61M 2025/109* (2013.01)

(58) Field of Classification Search
CPC ............... A61B 17/320758; A61B 2017/2212; A61B 2017/22051; A61B 2017/22054; A61B 17/320708; A61B 17/320725; A61B 17/32075; A61B 17/320783; A61B 2017/320716; A61B 2017/320733; A61B 2017/320791; A61B 17/3207; A61M 2025/109; A61M 25/1011; A61M 25/1004; A61M 2025/1015; A61M 2025/1043; A61M 2025/105; A61M 2025/1052
See application file for complete search history.

(56) References Cited

U.S. PATENT DOCUMENTS

| 5,284,486 | A | 2/1994 | Kotula et al. |
|---|---|---|---|
| 5,320,634 | A * | 6/1994 | Vigil .............. A61B 17/320725 604/103.08 |
| 5,569,275 | A | 10/1996 | Kotula et al. |
| 5,662,671 | A | 9/1997 | Barbut et al. |
| 5,779,721 | A | 7/1998 | Nash |
| 6,152,909 | A | 11/2000 | Bagaoisan et al. |
| 6,508,782 | B1 | 1/2003 | Evans et al. |
| 6,663,613 | B1 | 12/2003 | Evans et al. |
| 6,805,692 | B2 | 10/2004 | Muni et al. |

(Continued)

*Primary Examiner* — Julian W Woo
*Assistant Examiner* — Lucas Paez
(74) *Attorney, Agent, or Firm* — Liell & McNeil (57) ABSTRACT

A clot removal system includes first and second barriers that each have an expanded configuration forming an occlusion within a vessel and a collapsed configuration. At least one deployment device distally deploys the first barrier relative to a clot, and proximally deploys the second barrier relative to the clot. The at least one deployment device also delivers a thrombolytic agent into an isolated segment defined at least in part by the first and second barriers in the expanded configurations, and positions an impeller within the isolated segment. The impeller includes a substantially cylindrical hub having at least two impeller blades attached to rotate with the cylindrical hub. Each of the at least two impeller blades has a proximal end attached to the cylindrical hub and a distal end attached to the cylindrical hub. The impeller has a transport configuration in which the at least two impeller blades are moved toward the cylindrical hub and a deployed configuration in which the at least two impeller blades are moved away from the cylindrical hub.

17 Claims, 5 Drawing Sheets

(56) References Cited

U.S. PATENT DOCUMENTS

| | | | |
|---|---|---|---|
| 6,818,001 B2 * | 11/2004 | Wulfman et al. | 606/159 |
| 6,824,551 B2 | 11/2004 | Trerotola | |
| 6,929,633 B2 * | 8/2005 | Evans et al. | 604/509 |
| 7,329,267 B2 * | 2/2008 | Weber | A61B 17/320725 600/564 |
| 7,645,290 B2 | 1/2010 | Lucas | |
| 2002/0177800 A1 | 11/2002 | Bagaoisan et al. | |
| 2008/0208245 A1 * | 8/2008 | Hoffman | 606/200 |
| 2009/0254038 A1 | 10/2009 | Lapeyre | |

\* cited by examiner

CLOT REMOVAL SYSTEM AND METHOD

RELATION TO OTHER PATENT APPLICATION

This application claims priority to provisional patent application 61/552,535, filed Oct. 28, 2011, with the same title.

TECHNICAL FIELD

The present disclosure relates generally to a clot removal system, and more particularly to a clot removal system including at least one deployment device deploying first and second barriers, a thrombolytic agent, and an impeller including a cylindrical hub having at least two impeller blades.

BACKGROUND

Thrombosis is the formation of a thrombus, or blood clot, within the vascular system of a patient. A blood clot typically occurs when blood hardens from a liquid to a solid. When attached to vessel walls, blood clots, and other substances, such as plaque or fat, may reduce or block blood flow downstream from the clot. This partially or completely blocked blood flow may prevent normal blood flow and oxygen from reaching certain tissues and, thus, may result in damage to the tissues. If a clot becomes dislodged from the vessel walls it may travel to other portions of the vascular system, where it may ultimately occlude critical blood flow. Regardless of the particular location of the clot within the vascular system, clots consisting of blood or other substances, if left untreated, may cause serious damage and, in some cases, may become life threatening.

A wide variety of invasive and non-invasive techniques are available for breaking up and/or removing clots within the vascular system. For example, some techniques include the use of pharmacological agents, also referred to as thrombolytic agents, to help dissolve the clots. Other techniques may include the use of mechanical agitation to dislodge clots from walls of the vascular system. For example, some systems use a rotatable filter to break up the clot into smaller pieces. Portions of the clot dislodged from the vessel walls, according to some embodiments, may then be aspirated from the vascular system. A number of risks are associated with clot removal procedures, including risks associated with the use of thrombolytic agents and risks associated with the migration of dislodged portions of the clot. Further, there is a continuing need for clot removal systems that minimize these risks and more efficiently remove clots.

The present disclosure is directed toward one or more of the problems set forth above.

SUMMARY OF THE DISCLOSURE

In one aspect, a clot removal system includes first and second barriers that each have an expanded configuration forming an occlusion within a vessel and a collapsed configuration. At least one deployment device distally deploys the first barrier relative to a clot, and proximally deploys the second barrier relative to the clot. The at least one deployment device also delivers a thrombolytic agent into an isolated segment defined at least in part by the first and second barriers in the expanded configurations, and positions an impeller within the isolated segment. The impeller includes a substantially cylindrical hub having at least two impeller blades attached to rotate with the cylindrical hub. Each of the at least two impeller blades has a proximal end attached to the cylindrical hub and a distal end attached to the cylindrical hub. The impeller has a transport configuration in which the at least two impeller blades are moved toward the cylindrical hub and a deployed configuration in which the at least two impeller blades are moved away from the cylindrical hub.

In another aspect, a method for removing a clot from a patient vessel using a clot removal system includes distally deploying a first barrier relative to the clot using at least one deployment device, and proximally deploying a second barrier relative to the clot using the at least one deployment device. Each of the first and second barriers is moved from a collapsed configuration to an expanded configuration that forms an occlusion within the patient vessel. A thrombolytic agent is delivered into an isolated segment defined by the first and second barriers in the expanded configurations using the at least one deployment device. An impeller is positioned within the isolated segment by advancing the impeller through the at least one deployment device in a transport configuration in which an inner wall of the deployment device moves impeller blades of the impeller toward a cylindrical hub of the impeller. The impeller is then advanced distally beyond an open end of the deployment device to allow the impeller to move into a deployed configuration in which the impeller blades are moved away from the cylindrical hub. A spiral fluid flow within the isolated segment is induced by rotating the impeller blades with the cylindrical hub. The method also includes dissolving the clot using the thrombolytic agent, and dislodging a portion of the clot from a vessel wall using a scraping edge of each of the impeller blades. Each of the impeller blades has a proximal end attached to the cylindrical hub and a distal end attached to the cylindrical hub.

DETAILED DESCRIPTION

Figure 1:
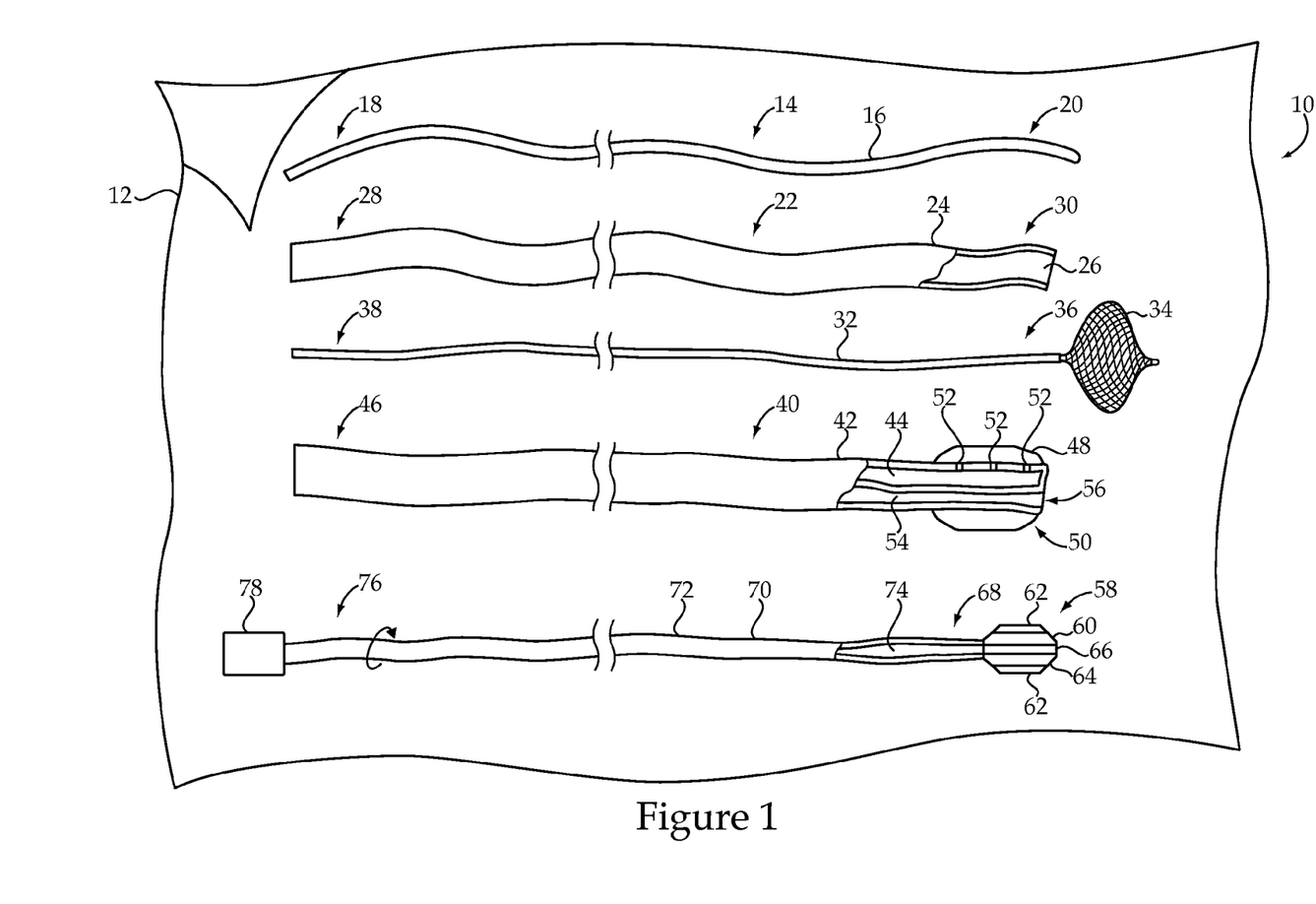
FIG. 1 is a partially sectioned side diagrammatic view of a clot removal system, according to one embodiment of the present disclosure.

Referring to FIG. 1, there is shown a clot removal system 10 according to one embodiment of the present disclosure. The clot removal system 10 may include a number of components, which may be provided within a sterile, tear open package 12, as is known in the art. In performing a clot removal procedure on a patient, some or all of the components of the clot removal system 10 may be used, depending upon the specifics of the procedure to be performed. As should be appreciated, however, the components shown in FIG. 1 might be separately packaged and/or the clot removal system 10 might also include components in addition to those shown, including components routinely used in percutaneous vascular procedures.

The clot removal system 10 may include at least one wire guide 14, which is a device commonly used in vascular procedures to introduce a wide variety of medical devices into the vascular system. Generally speaking, wire guide 14 includes an elongate flexible body 16 extending from a proximal end 18 to a distal end 20. Since wire guides are known, wire guide 14 will not be discussed herein in greater detail. However, it should be noted that wire guide 14 may be made from any of a number of known materials commonly used to manufacture medical devices and may include any of a variety of known configurations. For example, some wire guides include an elongate core element with one or more tapered sections near a distal end thereof. A flexible helical coil may be disposed about at least a distal portion, such as a tapered portion, of the core element. In the present disclosure, "proximal" will be used to refer to the end of a component or feature that is closest to a clinician, while "distal" is used to refer to a component or feature that is farthest away from the clinician. Such meanings are consistent with conventional use of the terms and, as such, should be understood by those skilled in the art.

At least one deployment device may be provided with the clot removal system 10. As shown in the exemplary embodiment, the clot removal system 10 may also include a first catheter, or sheath, 22, which may function as a deployment device for the clot removal system 10. The first catheter 22 generally includes an elongate tubular body 24 defining a lumen 26 extending from an open proximal end 28 to an open distal end 30 of the elongate tubular body 24. The elongate tubular body 24 may be made from any common medical tube material, such as, for example, a plastic, rubber, silicone, or Teflon® material, and may exhibit both stiffness, or firmness, and flexibility. Materials as well as dimensions may vary depending on the particular application.

The coil delivery system 10 may also include a mesh deployment wire 32 having a self-expanding mesh 34 disposed at a distal end 36 thereof. The mesh deployment wire 32 may or may not be disposed at a center of the self-expanding mesh 34. The mesh deployment wire 32 may be made from any known material and, according to some embodiments, may be made from or may include a reinforcement, such as a metal braid or coil, to provide kink resistance and torqueability, while retaining an adequate level of flexibility. According to one example, the self-expanding mesh 34 may be made from nitinol and may be covered with a Pellathane® material, a Thoralon® material, and/or silicone. The mesh deployment wire 32 must have adequate pushability such that a proximal end 38 may be manipulated by a clinician to deploy the self-expanding mesh 34 within a patient vessel. More specifically, the self-expanding mesh 34 may be deployed within the vascular system by advancing the mesh deployment wire 32 and self-expanding mesh 34 through the first catheter 22 such that the self-expanding mesh 34 advances through the open distal end 30 of the first catheter 30 and expands. When deployed, the self-expanding mesh 34 may function as a first barrier, as will be discussed below. The self-expanding mesh 34 may preferably have a non-porous coating, such as, for example, a Thoralon® coating, to reduce a fluid flow therethrough.

A second catheter 40 or, more specifically, a balloon catheter or sheath may also be provided and may function, at least in part, as a deployment device. The balloon catheter 40 may be similar in construction to the first catheter 22 and may include an elongate tubular body 42 defining at least one lumen. For example, the balloon catheter 40 may include an inflation lumen 44 extending from an open proximal end 46 to an inflation balloon 48 mounted on a distal end 50 of the balloon catheter 40. The inflation lumen 44 may be in fluid communication with the interior of the inflation balloon 48 via openings 52 through the elongate tubular body 42. Thus, as should be appreciated, a fluid source may be used to inflate the inflation balloon 48 via the inflation lumen 44. When inflated, or deployed, the inflation balloon 48 may function as a second barrier, as will be discussed below. The balloon catheter 40 may also include a device lumen 54, which is separate from the inflation lumen 44 and may extend from the open proximal end 46 to an opening 56 through the distal end 50 of the balloon catheter 40. The device lumen 54 may be used for deploying additional devices and/or thrombolytic agents of the clot removal system 10. Further, as will be discussed below, dislodged clots may be removed, such as by aspiration, through the device lumen 54.

The clot removal system 10 also includes an impeller 58. The impeller 58 generally includes a cylindrical hub 60 having at least two impeller blades 62 extending radially therefrom, with the impeller blades 62 being attached to rotate with the cylindrical hub 60. According to the exemplary embodiment, the cylindrical hub 60 includes a hollow housing 64 defining an opening 66 therethrough. As shown, the impeller 58 is disposed at a distal end 68 of a hollow cable 70. The hollow cable 70 may be made from any of a variety of medical grade materials and may generally include an elongate tubular body 72 defining a lumen 74 extending from a proximal end 76 to the distal end 68. The opening 66 of the hollow housing 64 and the lumen 74 of the hollow cable 70 are aligned, and in fluid communication, such that the impeller 58 and hollow cable 70 may be inserted into the vascular system over a wire, such as the mesh deployment wire 32. Although the hollow cable 70 and, thus, impeller 58 may be manually rotated, a drive unit 78 may be attached at or near the proximal end 76 of the hollow cable 70 for rotating the hollow cable 70 and impeller 58. According to some embodiments, the hollow cable 70 may be coated with a Teflon® material or may be otherwise slip-coated to enhance rotation. The impeller 58, and/or the other components of the clot removal system 10, may include one or more radiopaque markers to facilitate visibility during imaging of the procedure.

Figure 2:
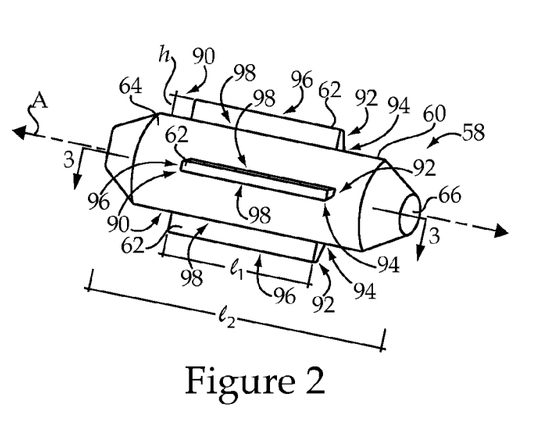
FIG. 2 is a perspective view of an impeller of the clot removal system of FIG. 1, according to one embodiment of the present disclosure, shown in a deployed configuration.

Turning now to FIG. 2, the impeller 58 will be discussed in greater detail. According to the exemplary embodiment, each of the impeller blades 62 has a proximal end 90 attached to the cylindrical hub 60 and a distal end 92 attached to the cylindrical hub 60. Each impeller blade 62 may be attached at an attachment edge 94 and may include a substantially continuous and planar surface extending radially outward from the attachment edge and terminating at a scraping edge 96. More specifically, each impeller blade 62 may have opposing surfaces 98 that are substantially continuous and planar. An axial length $l_1$, relative to axis A, of each of the impeller blades 62 may be greater than a radial height h. Further, the cylindrical hub 60 may extend continuously along the axial length $l_1$ of each of the impeller blades 62 and may extend both proximally and distally beyond each of the impeller blades 62. Specifically, the cylindrical hub 60 may have an axial length $l_2$ that is greater than the axial length $l_1$ of the impeller blades 62.

Figure 3:
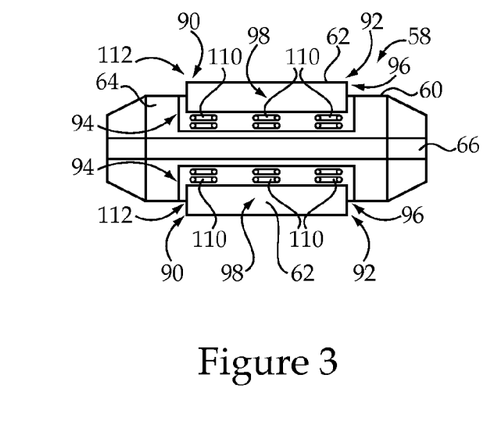
FIG. 3 is a cross sectional view of the impeller of FIG. 2 taken along lines 3-3, shown in a transport configuration, according to another aspect of the present disclosure.

The impeller 58 is shown in a deployed configuration in FIG. 2, in which the impeller blades 62 are moved away from the cylindrical hub 60. Turning now to FIG. 3, the impeller 58 may also have a transport configuration in which the impeller blades 62 are at least partially retracted within the cylindrical hub 60. Springs 110, or other biasing means, positioned within slots 112 of the cylindrical hub 60 may interconnect the attachment edge 94 and cylindrical hub 60 and may be used to bias the impeller 58 or, more specifically, the impeller blades 62 toward the deployed configuration. A deployment device, such as the balloon catheter 40 described above may be used to deploy the impeller 58. Specifically, for example, walls defining the device lumen 54 of the balloon catheter 40 may urge the impeller blades 62 into slots 112, against the bias of springs 110, and into the transport configuration. When the impeller 58 is advanced through the opening 56 at the distal end 50 of the balloon catheter 40, the springs 110 may urge the impeller blades 62 radially outward and, thus, move the impeller 58 into the deployed configuration, as shown in FIG. 2.

Figure 4:
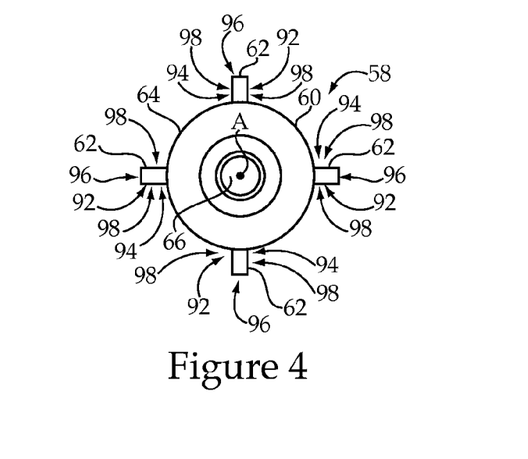
FIG. 4 is an end view of the impeller shown in FIGS. 2 and 3, shown in the deployed configuration, according to another aspect of the present disclosure.

Turning now to FIG. 4, an end view of the impeller 58 is shown. As shown in the exemplary embodiment, the impeller 58 may include four impeller blades 62, although any desired number of impeller blades 62 may be used. Although not required, the impeller blades 62 may be oriented substantially parallel to the axis of rotation A. An outer diameter of the impeller 58 in a deployed configuration, as shown in FIG. 4, may be sized to match an inner diameter of a patient vessel, the benefits of which will be described below. It should be appreciated that an outer diameter of the impeller 58 in the transport configuration, shown in FIG. 3, may be sized to match, or easily advance through, an inner diameter of a deployment device, such as the device lumen 54 of the balloon catheter 40.

Figure 5:
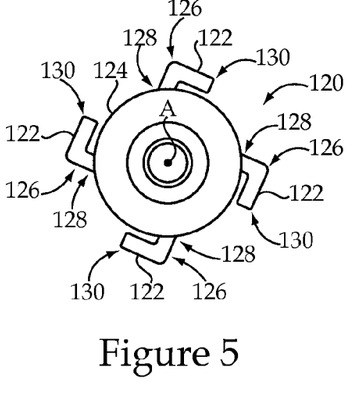
FIG. 5 is an end view of an alternative embodiment of an impeller, shown in a transport configuration, according to another aspect of the present disclosure.

Turning now to FIG. 5, an alternative impeller 120 is shown having an alternative attachment means and alternative configurations. Specifically, impeller 120 may include impeller blades 122 attached to a cylindrical hub 124 via living hinges 126. Specifically, attachment edges 128 of the impeller blades 122 may be fixedly attached to the cylindrical hub 124, while scraping edges 130 may be movable about the living hinges 126. While a deployed configuration of the impeller 120 may have an end view similar to that of FIG. 4, in which the scraping edges 130 are biased radially outward relative to attachment edges 128, a transport configuration may include the scraping edges 130 folded toward the cylindrical hub 124 about the living hinges 126. According to such an embodiment, it may be important to consider movement of the scraping edges 130 relative to the living hinges 126 when selecting a direction of rotation about axis A.

Figure 6:
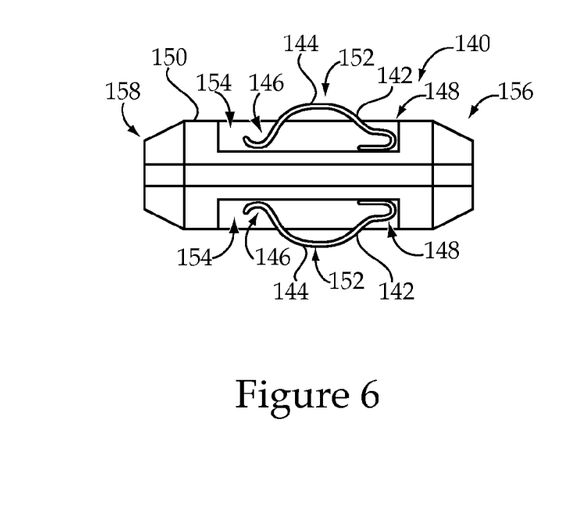
FIG. 6 is a cross sectional view of another alternative embodiment of an impeller, shown in a deployed configuration, according to another aspect of the present disclosure.

According to another alternative embodiment shown in FIG. 6, an impeller 140 for use with the clot removal system 10 disclosed herein may include impeller blades 142 that function similar to tension springs. Thus, the impeller blades 142, rather than having substantially continuous and planar opposing surfaces, as shown in previous embodiments, may comprise a tension spring body 144 that is attached at both a proximal end 146 and a distal end 148 to a cylindrical hub 150. As used herein, at least with respect to the current embodiment, "attached" may include contact, such as biased contact, with another component. For example, the distal end 148 of the impeller blade 142 may have a fixed attachment, such as an attachment using adhesion, welding, bonding, etc., while the proximal end 146 may have a biased attachment in which the proximal end 146 is urged into contact with the cylindrical hub 150.

Figure 7:
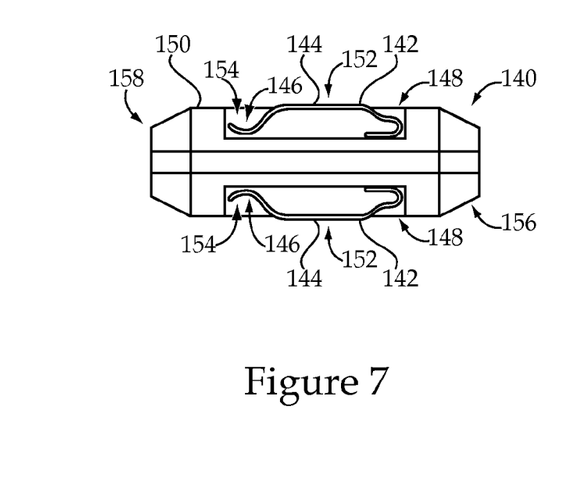
FIG. 7 is a cross sectional view of the impeller of FIG. 6, shown in a transport configuration, according to another aspect of the present disclosure.

The impeller 140 is shown in a deployed configuration in FIG. 6, in which the impeller blades 142 are moved away from the cylindrical hub 150. Turning now to FIG. 7, the impeller 140 may also have a transport configuration in which the impeller blades 142 are at least partially retracted within the cylindrical hub 150. As stated above, the impeller blades 142 may each include a tension spring body 144 that is naturally biased to the deployed configuration, in which at least a central portion 152 of the tension spring body 144 is moved away from the cylindrical hub 150. A deployment device, such as the balloon catheter 40 described above may be used to deploy the impeller 140. Specifically, for example, walls defining the device lumen 54 of the balloon catheter 40 may urge the impeller blades 142 or, more specifically, the central portions 152 into slots 154, against the bias of the tension spring body 144, and into the transport configuration. As shown, the proximal end 146 of each impeller blade 142 may move toward a distal end 156 of the cylindrical hub 150 in the deployed configuration of FIG. 6 and toward a proximal end 158 of the cylindrical hub 150 in the transport configuration of FIG. 7. It should be appreciated that the slots 154 may be optional and may be incorporated to reduce the profile of the impeller 140.

Figure 8:
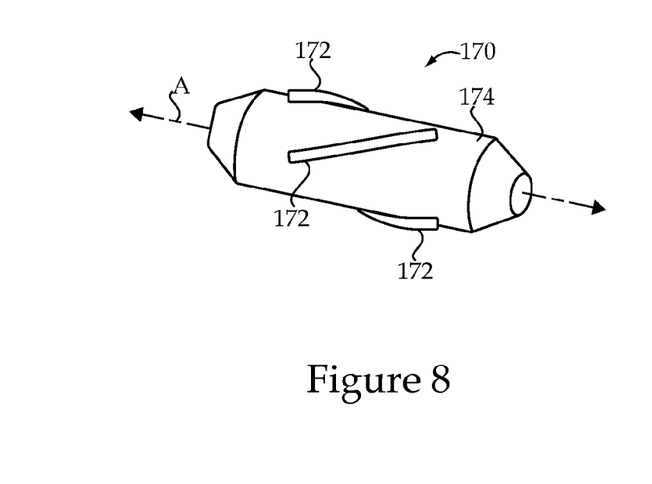
FIG. 8 is a perspective view of yet another alternative embodiment of an impeller, shown in a deployed configuration, according to another aspect of the present disclosure.
Figure 9:
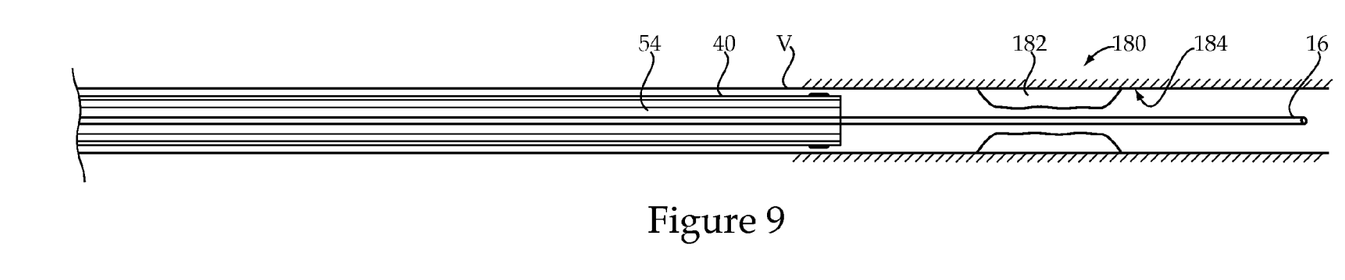
FIG. 9 is a side diagrammatic view of a vascular structure of a patient at one stage of a clot removal procedure, according to another aspect of the present disclosure.

According to another alternative impeller 170, shown in FIG. 8, impeller blades 172 may be oriented at an angle relative to the axis of rotation A, and may be attached to a cylindrical hub 174 using any known attachment means. For example, impeller blades 172 may be interconnected with the cylindrical hub 174 through springs, or other similar biasing means, as described above. Alternatively, however, the attachment may include the use of adhesion, force convection heating, radio frequency heating, ultrasonic welding, laser bonding, or any other known attachment means.

It should be appreciated that any of the impeller blades described herein, when rotated with a cylindrical hub, may induce a swirl fluid flow. Impeller blades oriented parallel to the axis of rotation A may induce a swirl fluid flow that is different than impeller blades oriented at various angles relative to the axis of rotation A. Thus, modifications to the size, shape, and configuration of the impeller blades are contemplated to alter the swirl fluid flow produced by the impeller. Modifications to the means for providing a deployed configuration and a transport configuration, and resulting dimensions of the impeller, are also contemplated to meet various procedural requirements.

The clot removal system 10 may also include a thrombolytic agent, or pharmacological agent, that breaks down clots. Exemplary thrombolytic agents may include streptokinase, urokinase, tissue plasminogen activators (tPA), and other similar agents. The thrombolytic agent may be used in conjunction with other components of the clot removal system 10 to break down and remove a clot within the vascular system of a patient. An exemplary clot removal procedure will be discussed in detail below.

INDUSTRIAL APPLICABILITY

The present disclosure is generally applicable to medical devices for use in percutaneous vascular procedures, or other procedures involving cavities, ducts, or canals of a patient. More specifically, the present disclosure is applicable to systems and methods for removing clots, which may include, blood clots, plaque, fat, and other clot forming materials, from the vascular system of a patient. Yet further, the present disclosure may be specifically applicable to clot removal systems including mechanical and pharmacological breakdown of clots.

Referring to FIGS. 9-14, a percutaneous vascular procedure using the clot removal system 10 of FIG. 1 will be described with reference to a vascular structure V of a patient. Although not shown, a clinician may position a needle, or introducer, through the skin of a patient to gain access to the vascular structure V. At a first stage of the procedure, a clinician may insert the wire guide 16 through a tube of the introducer and into the vascular structure V. The wire guide 16 may be placed across a thrombosed section 180 of the vascular structure V. More specifically, the wire guide 16 may be placed across a clot 182 attached to walls 184 of the vascular structure V. At this stage, or later in the procedure, the balloon catheter 40 or, more specifically, the device lumen 54 of the balloon catheter 40 may be introduced over the wire guide 16.

Figure 10:
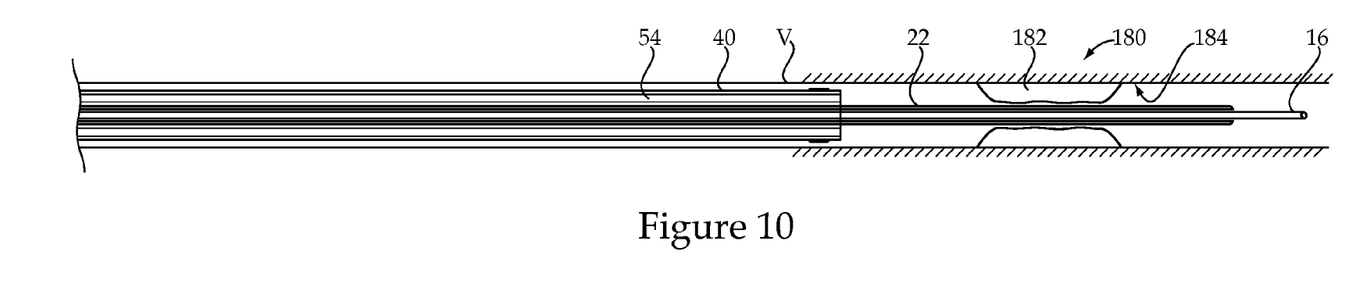
FIG. 10 is a side diagrammatic view of the vascular structure of a patient at another stage of a clot removal procedure, according to another aspect of the present disclosure.
Figure 11:
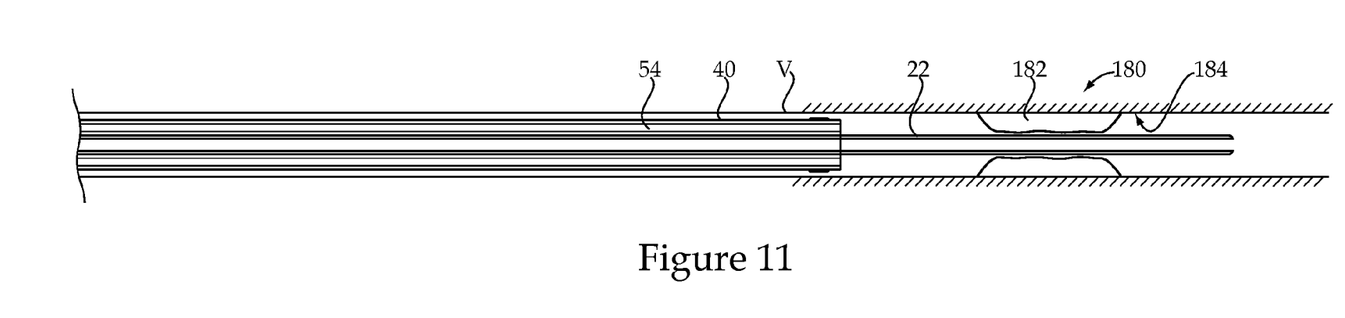
FIG. 11 is a side diagrammatic view of the vascular structure of a patient at another stage of a clot removal procedure, according to another aspect of the present disclosure.

Turning now to FIG. 10, another stage of the clot removal procedure is shown. At this stage, the first catheter 22, or first deployment device, may be delivered over the wire guide 16 and through the device lumen 54 of the balloon catheter 40. Alternatively, if the balloon catheter 40 is not yet inserted, the first catheter 22 may simply be introduced over the wire guide 16. After the first catheter 22 has been inserted into the vascular structure V, the wire guide 16 may be removed, as shown in FIG. 11.

Figure 12:
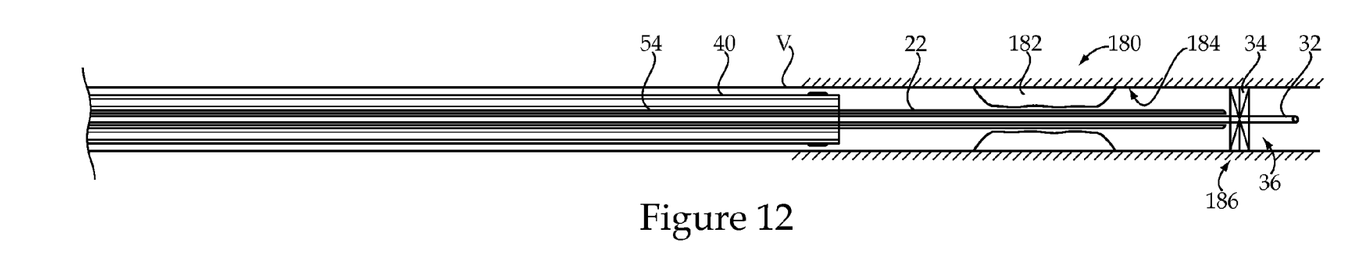
FIG. 12 is a side diagrammatic view of the vascular structure of a patient at another stage of a clot removal procedure, according to another aspect of the present disclosure.

As shown in FIG. 12, the mesh deployment wire 32 having the self-expanding mesh 34 disposed at the distal end 36 thereof is deployed through the first catheter 22. Specifically, the self-expanding mesh 34 is distally deployed relative to the clot 182 by advancing the mesh deployment wire 32 through the first catheter 22 such that the self-expanding mesh 34 advances through the open distal end 30 of the first catheter 22 and expands. When expanded, the self-expanding mesh 34 forms a first barrier 186 with the vascular structure V. A fluid flow through the self-expanding mesh 34 may be reduced using a non-porous coating on the self-expanding mesh 34. After the self-expanding mesh 34 is deployed, the first catheter 22 may be removed, as shown in FIG. 13.

Figure 13:
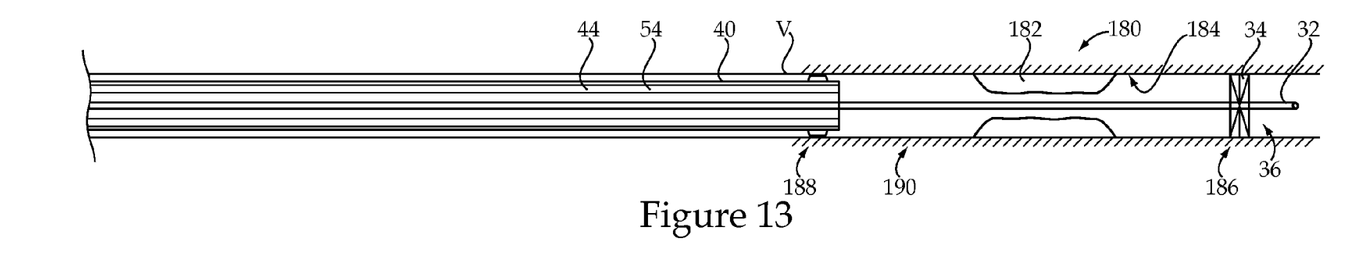
FIG. 13 is a side diagrammatic view of the vascular structure of a patient at another stage of a clot removal procedure, according to another aspect of the present disclosure.

Next, as shown in FIG. 13, a second barrier 188 may be proximally deployed relative to the clot 182. More specifically, the inflation balloon 48 of the balloon catheter 40 may be inflated using the inflation lumen 44, which is in fluid communication with a fluid source. The inflation balloon 48, when inflated or deployed, may function as the second barrier 188. It should be appreciated that if the balloon catheter was not previously inserted, this stage may include advancing the device lumen 54 over the mesh deployment wire 32 such that the inflation balloon 48 is proximally positioned relative to the clot 182. The first and second barriers 186 and 188, along with the walls 184 of the vascular structure V, form an isolated segment 190. Although alternative components or devices may be used in place of the specific first and second barriers 186 and 188 provided herein, it should be appreciated that the selected components preferably have collapsed configurations, such as those shown in FIG. 1 with respect to barriers 186 and 188, and expanded configurations, such as those shown in FIGS. 13 and 14, in which the barriers form occlusions within the vascular structure V. The collapsed configurations may correspond to deployment or advancement of the barriers 186 and 188 through the vascular structure V, while the expanded configurations may correspond to the preferred positions of the barriers 186 and 188 during the clot removal procedure. For example, for reasons stated herein, it may be desirable for the barriers 186 and 188 to form the isolated segment 190.

Figure 14:
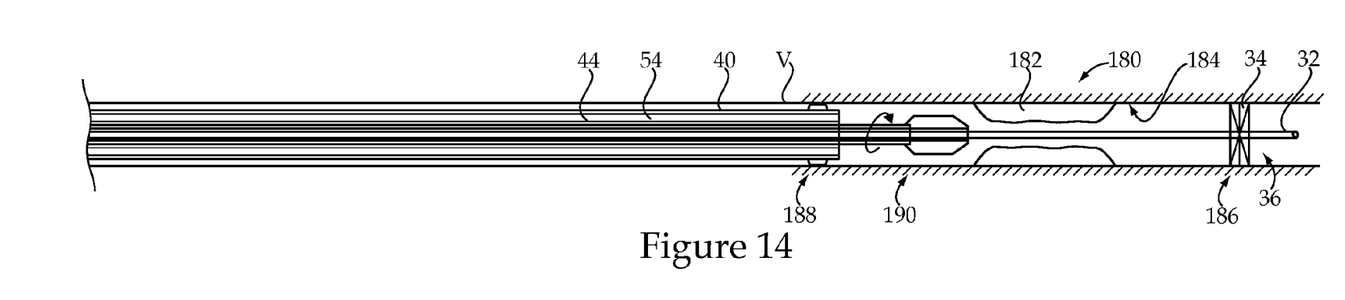
FIG. 14 is a side diagrammatic view of the vascular structure of a patient at another stage of a clot removal procedure, according to another aspect of the present disclosure.

Turning now to FIG. 14, the impeller 58 may be positioned within the isolated segment 190 by advancing the impeller 58 and hollow cable 70 through the device lumen 54 of the balloon catheter 40. Further, according to the exemplary embodiment, the hollow housing 64 and hollow cable 70 may be advanced over the mesh deployment wire 32 and through the device lumen 54. More specifically, the impeller 58 may be advanced through the balloon catheter 40 in the transport configuration of FIG. 3, in which walls of the device lumen 54 move the impeller blades 62 toward the cylindrical hub 60. The impeller 58 may then be advanced distally beyond the opening 56 of the balloon catheter 40 such that the impeller 58 moves to the deployed configuration of FIG. 2. In the deployed configuration, the impeller blades 62 are moved away from the cylindrical hub 60. It should be appreciated that any of the impeller embodiments disclosed or contemplated herein may be used with the clot removal system 10.

A thrombolytic agent, such as, for example, streptokinase, urokinase, or tPA, may be delivered into the isolated segment 190 through device lumen 54 of the balloon catheter 40. The thrombolytic agent may be used to dissolve the clot 182. A spiral fluid flow within the isolated segment 190 may be induced by rotating the cylindrical hub 60 and impeller blades 62, such as by rotating the hollow cable 70 using the drive unit 78. The spiral fluid flow, which may vary depending on the impeller embodiment that is selected, may improve distribution of the thrombolytic agent relative to the clot 182 and, thus, enhance the effectiveness of the thrombolytic agent in dissolving the clot 182. For example, it may be desirable for more of the thrombolytic agent to reach more surface area of the clot 182.

The first and second barriers 186 and 188 function to reduce the amount of thrombolytic agent that may travel past the barriers 186 and 188 and beyond the isolated segment 190 into other areas of the vascular system. It should be appreciated that the thrombolytic agent may cause unwanted bleeding in other areas of the vascular system and, thus, it may be desirable to restrict exposure of the thrombolytic agent to the isolated segment 190. Isolating the thrombolytic agent to precisely where it is needed may also allow a minimal amount of the thrombolytic agent to be used and, thus, may reduce costs of the procedure.

The impeller 58 also functions to dislodge the clot 182 or portions of the clot 182 from the walls 184 of the vascular structure V. Specifically, in the deployed configuration, the impeller blades 62 may be moved away from the cylindrical hub 60 such that the scraping edges 96, which have a significant axial length and may be attached to the cylindrical hub 60 at both ends 90, 92 or across an entire attachment edge 94, may contact the clot 182. It may be desirable for the outer diameter of the impeller 58, in the deployed configuration, to match, or be slightly less than, an inner diameter of the vascular structure V. A bias of the impeller blades 62 toward the deployed configuration may be selected such that the scraping edges 96 may scrape the clot 182 and, perhaps, walls 184 of the vascular structure V in an atraumatic fashion. It may be desirable during the clot removal procedure to move the impeller 58 proximally and distally within isolated segment 190 to maximize effectiveness.

Once a desirable portion of the clot 182 has been dislodged and/or dissolved, the impeller 58 may be removed by proximally retracting the hollow cable 70 and impeller 58 through the device lumen 54. Once the impeller 58 is removed, it may be desirable to aspirate fluid and clot fragments that have been confined to the isolated segment 190 using barriers 186 and 188 through the device lumen 54. The use of the mesh deployment wire 32, which may have a smaller outer diameter than an alternative barrier and/or deployment device, may maximize the amount of clot fragments that may be aspirated through the device lumen 54. The mesh deployment wire 32 and self-expanding mesh 34, which supports the impeller 58 thereon, may assist in centering the impeller 58 within the vascular structure V.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A clot removal system, comprising:
    first and second barriers, wherein each of the first and second barriers has an expanded configuration forming an occlusion within a vessel and a collapsed configuration;
    at least one deployment device for distally deploying the first barrier relative to a clot, proximally deploying the second barrier relative to the clot, and delivering a thrombolytic agent into an isolated segment defined by the first and second barriers in the expanded configurations; and
    an impeller including a cylindrical hub having at least two impeller blades attached to rotate with the cylindrical hub, wherein each of the at least two impeller blades has a proximal end attached to the cylindrical hub and a distal end attached to the cylindrical hub, wherein the impeller has a transport configuration in which the deployment device contacts and urges the at least two impeller blades toward being at least partially retracted within the cylindrical hub against a bias toward a deployed configuration in which the at least two impeller blades are out of contact with the deployment device and moved away from the cylindrical hub by action of the bias, wherein the at least one deployment device is used for positioning the impeller within the isolated segment.

2. The clot removal system of claim 1, wherein the cylindrical hub extends continuously along an axial length of each of the at least two impeller blades and extends both proximally and distally beyond each of the at least two impeller blades.

3. The clot removal system of claim 2, wherein the impeller has a consistent cross section along an axial length of the impeller.

4. The clot removal system of claim 2, wherein each of the at least two impeller blades has a continuous planar surface area extending from the cylindrical hub to a scraping edge of each of the at least two impeller blades.

5. The clot removal system of claim 4, wherein the axial length of each of the at least two impeller blades is greater than a radial height of each of the at least two impeller blades.

6. The clot removal system of claim 5, wherein the first barrier includes a self-expanding mesh having a non-porous coating, wherein the self-expanding mesh is attached at a distal end of a mesh deployment wire.

7. The clot removal system of claim 6, wherein the second barrier includes an inflatable balloon disposed on a distal end of a catheter.

8. The clot removal system of claim 7, wherein the cylindrical hub includes a hollow housing defining an opening therethrough and is disposed at a distal end of a hollow cable, wherein the hollow housing and hollow cable are advanced over the mesh deployment wire.

9. The clot removal system of claim 8, further including a drive unit attached at a proximal end of the hollow cable for rotating the hollow cable and impeller.

10. A method for removing a clot from a patient vessel using a clot removal system, comprising steps of:
    distally deploying a first barrier relative to the clot using at least one deployment device by moving the first barrier from a collapsed configuration to an expanded configuration which forms an occlusion within the patient vessel;
    proximally deploying a second barrier relative to the clot using the at least one deployment device by moving the second barrier from the collapsed configuration to the expanded configuration;
    delivering a thrombolytic agent into an isolated segment defined by the first and second barriers in the expanded configurations using the at least one deployment device;
    positioning an impeller within the isolated segment by advancing the impeller through the at least one deployment device in a transport configuration in which an inner wall of the deployment device contacts and urges the impeller blades of the impeller against a bias toward being at least partially retracted into a cylindrical hub of the impeller, and advancing the impeller distally beyond an open end of, and out of contact with, the deployment device to allow the impeller to move into a deployed configuration in which the impeller blades are moved away from the cylindrical hub by action of the bias;
    inducing a spiral fluid flow within the isolated segment by rotating the impeller blades with the cylindrical hub;
    dissolving the clot using the thrombolytic agent; and
    dislodging a portion of the clot from a vessel wall using a scraping edge of each of the impeller blades, wherein each of the impeller blades has a proximal end attached to the cylindrical hub and a distal end attached to the cylindrical hub.

11. The method of claim 10, further including selecting an impeller having an outer diameter in the deployed configuration matching an inner diameter of the patient vessel.

12. The method of claim 10, wherein distally deploying the first barrier includes advancing a mesh deployment wire having a self-expanding mesh disposed at a distal end thereof through a first catheter such that the self-expanding mesh advances through an open distal end of the first catheter and expands.

13. The method of claim 12, further including reducing a fluid flow through from the isolated segment through the self-expanding mesh using a non-porous coating on the self-expanding mesh.

14. The method of claim 12, wherein proximally deploying the second barrier includes advancing a device lumen of a second catheter over the mesh deployment wire and inflating a balloon disposed on a distal end of the second catheter using an inflation lumen of the second catheter.

15. The method of claim 14, further including advancing a hollow cable and a hollow housing of the cylindrical hub, which is disposed at a distal end of a hollow cable, over the mesh deployment wire and through the device lumen of the second catheter.

16. The method of claim 15, further including aspirating portions of the clot through the device lumen of the second catheter.

17. The method of claim 15, further including centering the impeller within the patient vessel using the mesh deployment wire and self-expanding mesh.

* * * * *